Figure 1:
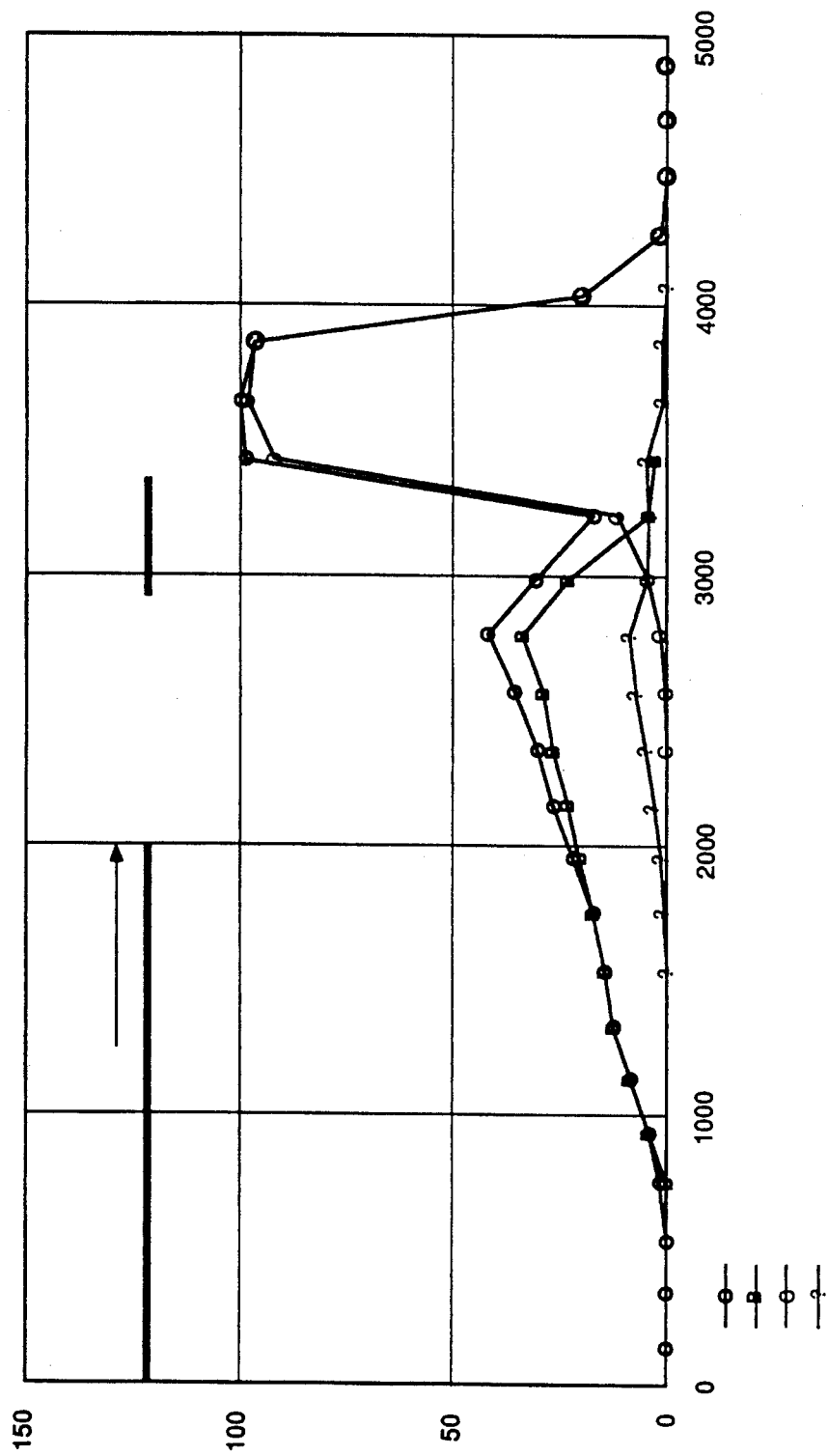

United States Patent [19]

Dobuler et al.

[11] Patent Number: 4,999,112
[45] Date of Patent: Mar. 12, 1991

[54] REMOVAL OF THIAMINE MONOPHOSPHATE FROM A SOLUTION OF THIAMINE

[75] Inventors: Walter Dobuler, Heidelberg; Wolfgang Schul, Ludwigshafen; Joachim Paust, Neuhofen; Alfred Mitschker, Odenthal-Holl, all of Fed. Rep. of Germany

[73] Assignee: BASF Aktiengesellschaft, Ludwigshafen, Fed. Rep. of Germany

[21] Appl. No.: 482,836

[22] Filed: Feb. 21, 1990

[30] Foreign Application Priority Data

Mar. 2, 1989 [JP] Japan ................................ 3906632

[51] Int. Cl.$^5$ ............................................. B01D 15/08
[52] U.S. Cl. .................................... 210/656; 210/670; 210/692; 544/243
[58] Field of Search ....................... 210/670, 692, 656; 544/243

[56] References Cited

U.S. PATENT DOCUMENTS 4,002,564  1/1977  Carbonel et al. .................... 210/688
4,472,169  9/1984  Shuttleworth .......................... 8/639

FOREIGN PATENT DOCUMENTS 166566  1/1986  European Pat. Off. .
201896  11/1986  European Pat. Off. .
311910  4/1989  European Pat. Off. .
1085527  7/1960  Fed. Rep. of Germany .

OTHER PUBLICATIONS

Journal of Applied Chemistry, vol. 8, 1958, p. 458, Faulkner, "Autoxidation of Methyl Elaeostearate".

Primary Examiner—Ivars Cintins
Attorney, Agent, or Firm—Oblon, Spivak, McClelland, Maier & Neustadt

[57] ABSTRACT

Thiamine monophosphate is separated from a solution of thiamine phosphates containing thiamine monophosphate and cocarboxylase and having a pH of 2–7 by using a cation exchanger resin having a $pK_u$ of 1.0–4.5.

6 Claims, 2 Drawing Sheets

REMOVAL OF THIAMINE MONOPHOSPHATE FROM A SOLUTION OF THIAMINE

The present invention relates to a process for removing thiamine monophosphate from a solution of thiamine phosphates which contains thiamine monophosphate and cocarboxylase as useful products by using a cation exchanger and eluting the thiamine monophosphate with an acid.

The phosphorylation of thiamine generally produces a mixture of the following composition: about 70% of thiamine monophosphate, about 20% of cocarboxylase (thiamine diphosphate) and about 5% of thiamine triphosphate and thiamine tetraphosphate. As described in DE-A-1 085 527, the mixture is customarily separated by first removing the phosphoric acid and then passing the mixture over a weakly basic ion exchanger. This eliminates residual amounts of phosphoric acid. The deacidified mixture is then passed over a strongly acidic ion exchanger, e.g. Amberlite® IR-120. Thiamine monophosphoric acid adheres, while the cocarboxylase and the higher phosphates, essentially thiamine tri- and tetraphosphate, are eluted. This procedure gives the cocarboxylase in the form of a very dilute solution, causing not inconsiderable evaporation costs. Furthermore, some of the cocarboxylase is hydrolysed by the strongly acid ion exchanger to thiamine monophosphate, which reduces the total yield of cocarboxylase. Instead of using a strongly acidic ion exchanger resin use is also made of a weakly acidic ion exchanger resin, e.g. Amberlite® IRC-50. This again represents a selective ion exchange process which likewise produces the eluted cocarboxylase in a highly dilute solution.

It is an object of the present invention to develop a process of the type mentioned at the beginning in such a way as to give significantly more efficient removal of thiamine monophosphate. Another object is that the solution of cocarboxylase obtained should not be very dilute.

We have found that these objects are achieved by a process of the type mentioned at the beginning, wherein a solution which contains the thiamine monophosphate and the cocarboxylase has a pH of 2-7 and the cation exchanger used has a $pK_a$ of 1.0-4.5.

The $pK_a$ of a cation exchanger is the apparent pK, which can be determined by the method of F. Helfferich, Ionenaustauscher, vol. 1, p. 84 (1959), Verlag Chemie GmbH, Weinheim, Bergstrabe.

In a preferred embodiment of the present invention, the cation exchanger resin used possesses iminodiacetic acid residues or aminoalkylene- and/or iminodialkylene-phosphonic acid residues as functional groups. It is particularly advantageous to use a cation exchanger resin possessing aminomethylene- and/or iminodimethylene-phosphonic acid residues as functional groups. It is similarly particularly advantageous to use a solution with a pH of 4.5-5.5. A particularly suitable eluent is aqueous 1-30% strength hydrochloric acid.

The cation exchanger resins with aminoalkyleneand/or iminoalkylene-phosphonic acid groups are polystyrene/divinyl polymers which preferably contain an aminomethylene- and/or iminomethylene-phosphonic acid group as functional group. Cation exchanger resins with aminoalkylene- and/or iminoalkylene-, in particular aminomethylene- and/or iminomethylene-phosphonic acid groups are known (cf. for example J. Appl. Chem. 8, (1958), 458; US-A-4 002 564; CA 93, 168909x) and are commercially available. It is particularly advantageous to use the cation exchanger resin with aminoalkylene- and/or iminoalkylene-phosphonic acid groups available from Bayer AG under the tradename Lewatit® OC 1060.

The cation exchanger resins with aminoalkylene- and/or iminoalkylene-phosphonic acid groups show particularly high selectivity and a surprisingly high capacity for thiamine monophosphate. If a solution which has the above composition and a pH of 2-7, preferably 4.5-5.5, is passed over these resins, the thiamine monophosphate is selectively adsorbed. The cocarboxylase and the higher phosphates are eluted in an eluate which in the course of the elution surprisingly becomes more and more concentrated. The process in question here is thus not a conventional exchange process but, surprisingly, a displacement chromatography process. The consequence is that the concentration of cocarboxylase in the eluate is equal to the concentration in the applied solution. The cocarboxylase can be isolated from the eluate in a conventional manner, for example by evaporation. The thiamine triphosphate and tetraphosphate are separated from the cocarboxylase by a conventional method.

Once the capacity of the ion exchanger is exhausted, it is rinsed with water and then with 1-30% strength aqueous HCl, preferably 7.5% strength HCl, as eluent. The thiamine monophosphate is eluted as a saturated solution in the form of the hydrochloride. After rinsing with water until neutral, the ion exchanger is ready again for use. This permits a rapid sequence of separating cycles in an industrial process. The capacity of Lewatit® OC-1060 is limited only by the proportion of thiamine monophosphate. For optimal separation, this capacity must not be exceeded. The capacity was found to be about 140 g of thiamine monophosphate/l of resin. According to the present invention it is thus possible to separate a solution of thiamine, thiamine monophosphate, cocarboxylase and higher phosphates in any desired composition by the above-described method without diluting the cocarboxylase yet selectively removing the thiaminemonophosphoric acid up to an amount of 140 g/l of Lewatit® OC-1060. The method has been successfully used to separate a mixture in which the cocarboxylase had already been concentrated to about 37% (see Example below).

The process according to the present invention has many advantages. For instance, the product concentration remains constant or even increases in the course of the purification step. In addition, the hydrochloric acid used as displacer restores the ion exchanger resin to its initial state, obviating the need for a separate regeneration step. The process according to the present invention also permits the industrially extremely important rapid sequence of separating cycles. A particular advantage is the fact that the resin capacity is high, being for example up to 140 g of thiamine monophosphate/l of resin in the case of Lewatit® OC-1060.

Figure 2:
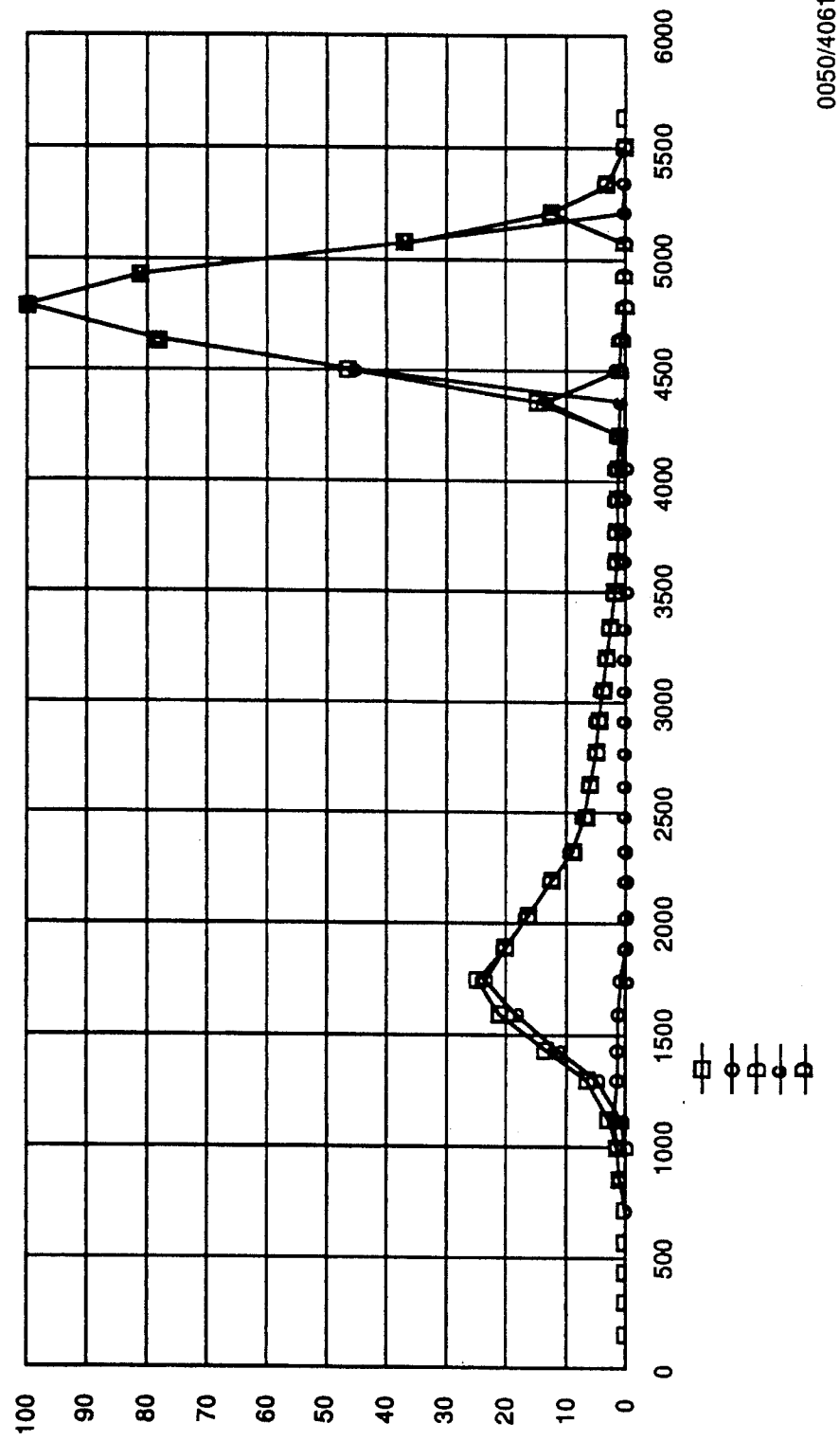

FIGS. 1 and 2 show elution diagrams of a separation according to the invention.

The present invention is further illustrated by the following Example:

EXAMPLE 2,000 g of a solution of the following composition, and pH 6 is applied to a separating column measuring 330 * 65 mm: Composition:

| | Amount in g | % share of dry substance | concentration in solution |
|---|---|---|---|
| Thiamine monophosphate | 150 | (57%) | 7.5% strength |
| Cocarboxylase | 95 | (36%) | 4.8% strength |
| Remainder (thiamine tri- and tetraphosphate) | 18 | (7%) | 0.9% strength |
| Dry substance | 263 | (100%) | 13.2% strength solution = 2,000 g of solution (about 2,000 ml) |

The following volumes were applied:

| | |
|---|---|
| Solution | 1.8 BV (1 BV = 1,100 ml; BV = bed volume) |
| Water | 1.0 BV |
| HCl 7.5% | 0.5 BV |
| Water | 2.2 BV |
| Total applied volume | 5.5 BV |

| The following fractions were obtained: | | |
|---|---|---|
| Prerun | 0.9 BV | |
| Cocarboxylase | 1.8 BV | 4.8% strength |
| Monophosphate | 1.0 BV | 13.5% strength |
| Afterrun | 1.8 BV | |
| Total volume of fractions | 5.5 BV | |

The result obtained is shown as a graph in FIG. 1. The run was carried out with the Lewatit ® OC-1060 at about 100% capacity for thiamine monophosphate. FIG. 1 is the elution diagram of the separation. It can be seen that the concentration of cocarboxylase in the eluate rises continuously as the mixture is being applied. The monophosphate starts to break through toward the end of the cocarboxylase elution peak. Following a short intermediate rinse, the application of HCl elutes the monophosphate in high purity and concentration. The elution peak is sharp; there is no tailing. Following a rinse phase of water, the next product mixture can be applied.

FIG. 2 is likewise an elution diagram of a separation The same resin Lewatit ® OC-1060 was used. However, it was loaded to only 50% of the capacity for thiamine monophosphate and with a solution of about 20% of cocarboxylase and 75% of thiamine monophosphate. Between the application of the solution and the eluating with HCl, the resin was rinsed with plenty of water. It was found in this connection that the monophosphate remained in a stable state on the resin despite the long rinse. The subsequent elution with hydrochloric acid takes place abruptly. The intermediate rinse with water makes it possible to purify the thiamine monophosphate thoroughly, and the eluate obtained is pure.

We claim:

1. In a process for removing thiamine monophosphate from a solution of thiamine phosphates which contains thiamine monophosphate and cocarboxylase by contacting said solution with a cation exchanger resin and eluting the thiamine monophosphate with an acid and the cation exchanger resin has a $pK_a$ of 1.0–4.5.

2. A process as claimed in claim 1, wherein said cation exchanger resin possesses iminodiacetic acid residues or aminoalkylene- and/or iminodialkylene-phosphonic acid residues as functional groups.

3. A process as claimed in claim 1, wherein said cation exchanger resin possesses aminomethylene- and/or imindiomethylene-phosphonic acid residues as functional groups.

4. A process as claimed in claim 1, wherein said solution has a pH of 4.5–5.5.

5. A process as claimed in claim 1, wherein the acid used for eluting the thiamine monophosphate is aqueous 1–30% strength hydrochloric acid.

6. In a process for removing thiamine monophosphate from a solution of thiamine phosphates which contain thiamine monophosphate and cocarboxylase by contacting said solution with a cation exchanger resin and eluting the thiamine monophosphate with aqueous hydrochloric acid, the improvement which comprises using a solution of pH 2–7 and a cation exchanger resin which has a $pK_a$ of 1.0–4.5, and which possesses iminodiacetic acid residues or aminoalkylene- and/or iminodialkylene-phosphonic acid residues as functional groups.

* * * * *

UNITED STATES PATENT AND TRADEMARK OFFICE
CERTIFICATE OF CORRECTION

PATENT NO. : 4,999,112

DATED : March 12, 1991

INVENTOR(S) : Walter Dobler et al.

It is certified that error appears in the above-identified patent and that said Letters Patent is hereby corrected as shown below:

ON TITLE PAGE: Item [75] and Item [30].

The first inventor's name is incorrect, should be, -- Walter Dobler--, and the Foreign Application Priority Data is incorrect, should be, --Mar. 2, 1989 [DE] Fed. Rep. of Germany ..................3906632--.

Signed and Sealed this

Thirteenth Day of October, 1992

*Attest:*

DOUGLAS B. COMER

*Attesting Officer*      *Acting Commissioner of Patents and Trademarks*